United States Patent
Isch

(10) Patent No.: US 10,905,438 B2
(45) Date of Patent: Feb. 2, 2021

(54) DRILL BITS AND METHODS FOR PREPARING BONE

(71) Applicant: Biomet Manufacturing, LLC, Warsaw, IN (US)

(72) Inventor: Bryce A. Isch, Warsaw, IN (US)

(73) Assignee: Bioniet Manufacturing, LLC, Warsaw, IN (US)

( * ) Notice: Subject to any disclaimer, the term of this patent is extended or adjusted under 35 U.S.C. 154(b) by 255 days.

(21) Appl. No.: 15/927,566

(22) Filed: Mar. 21, 2018

(65) Prior Publication Data
US 2018/0289376 A1   Oct. 11, 2018

Related U.S. Application Data

(60) Provisional application No. 62/482,331, filed on Apr. 6, 2017.

(51) Int. Cl.
| | |
|---|---|
| *A61B 17/16* | (2006.01) |
| *A61B 17/17* | (2006.01) |
| *A61B 17/84* | (2006.01) |
| *A61B 17/15* | (2006.01) |
| *A61B 17/064* | (2006.01) |

(52) U.S. Cl.
CPC ...... *A61B 17/1617* (2013.01); *A61B 17/1624* (2013.01); *A61B 17/1682* (2013.01); *A61B 17/1728* (2013.01); *A61B 17/1775* (2016.11); *A61B 17/848* (2013.01); *A61B 17/0642* (2013.01); *A61B 17/15* (2013.01); *A61B 17/162* (2013.01); *A61B 17/1637* (2013.01)

(58) Field of Classification Search
CPC .................. A61B 17/1617; A61B 17/1775
See application file for complete search history.

(56) References Cited

U.S. PATENT DOCUMENTS

| | | | | |
|---|---|---|---|---|
| 3,602,218 A | * | 8/1971 | Riordan | A61B 17/68 606/916 |
| 5,300,077 A | * | 4/1994 | Howell | A61B 17/1714 606/79 |
| 7,641,677 B2 | * | 1/2010 | Weiner | A61B 17/685 411/389 |
| 8,808,338 B2 | * | 8/2014 | Martin | A61B 17/1717 606/316 |
| 2008/0086139 A1 | * | 4/2008 | Bourke | A61B 17/68 606/270 |

* cited by examiner

*Primary Examiner* — Christian A Sevilla
(74) *Attorney, Agent, or Firm* — Schwegman Lundberg & Woessner, P.A.

(57) ABSTRACT

Described herein are examples of orthopedic drill bits and methods of preparing a bone of a living being for fixation. An example method includes coupling a drive attachment of a drill bit to a mounting attachment of a driver, and placing a guide at a desired location on the bone. The guide has an opening corresponding to an area of bone to be removed. The guide provides proper positioning and alignment for drilling a hole. With the guide in place, the method further includes aligning the drill bit with the opening on the guide and drilling a hole in the bone. Once the hole is drilled, the method includes de-coupling the drill bit from the driver, and bending the drill bit at the drive attachment while the drill bit is still in the bone. In some examples, additional method steps follow preparation of the hole.

19 Claims, 13 Drawing Sheets

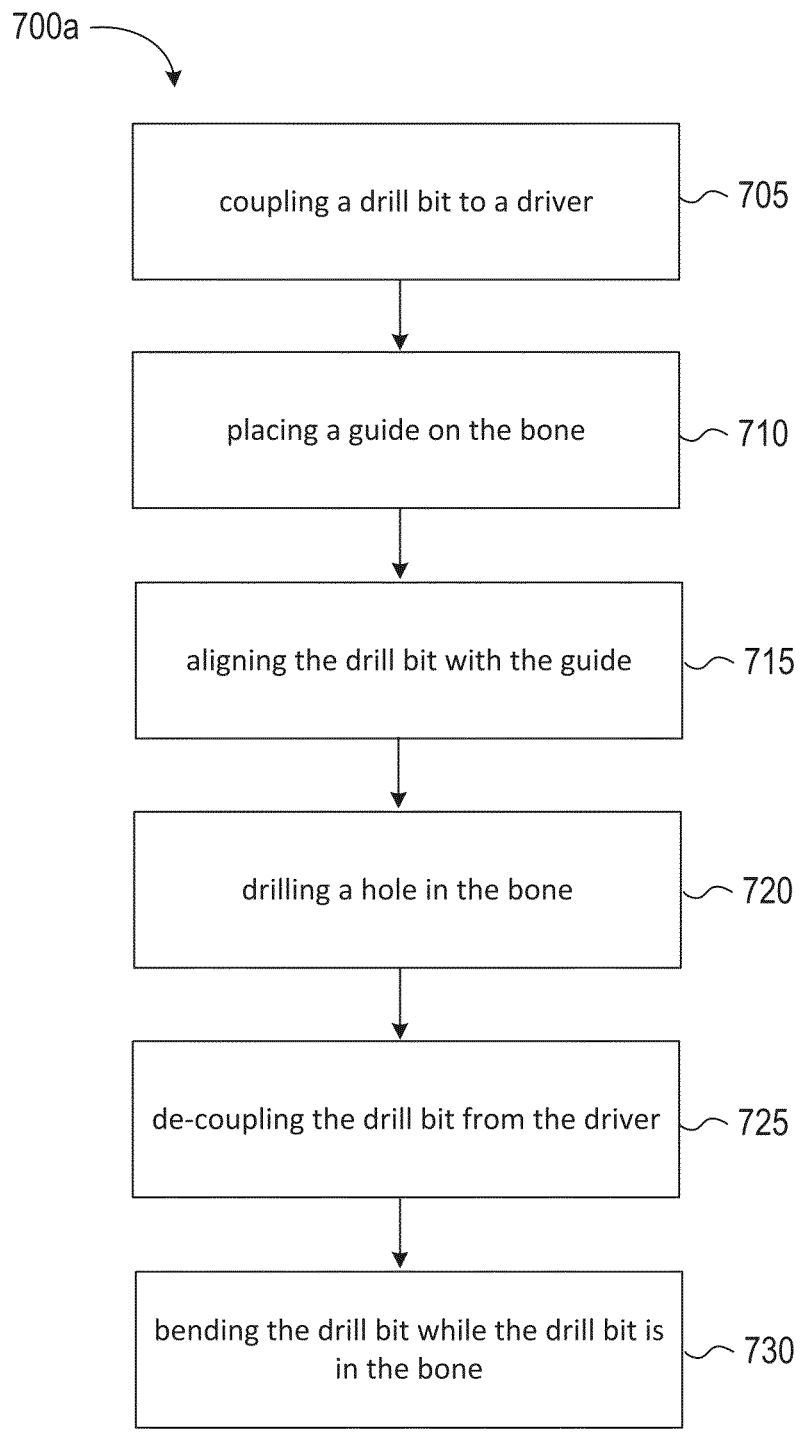

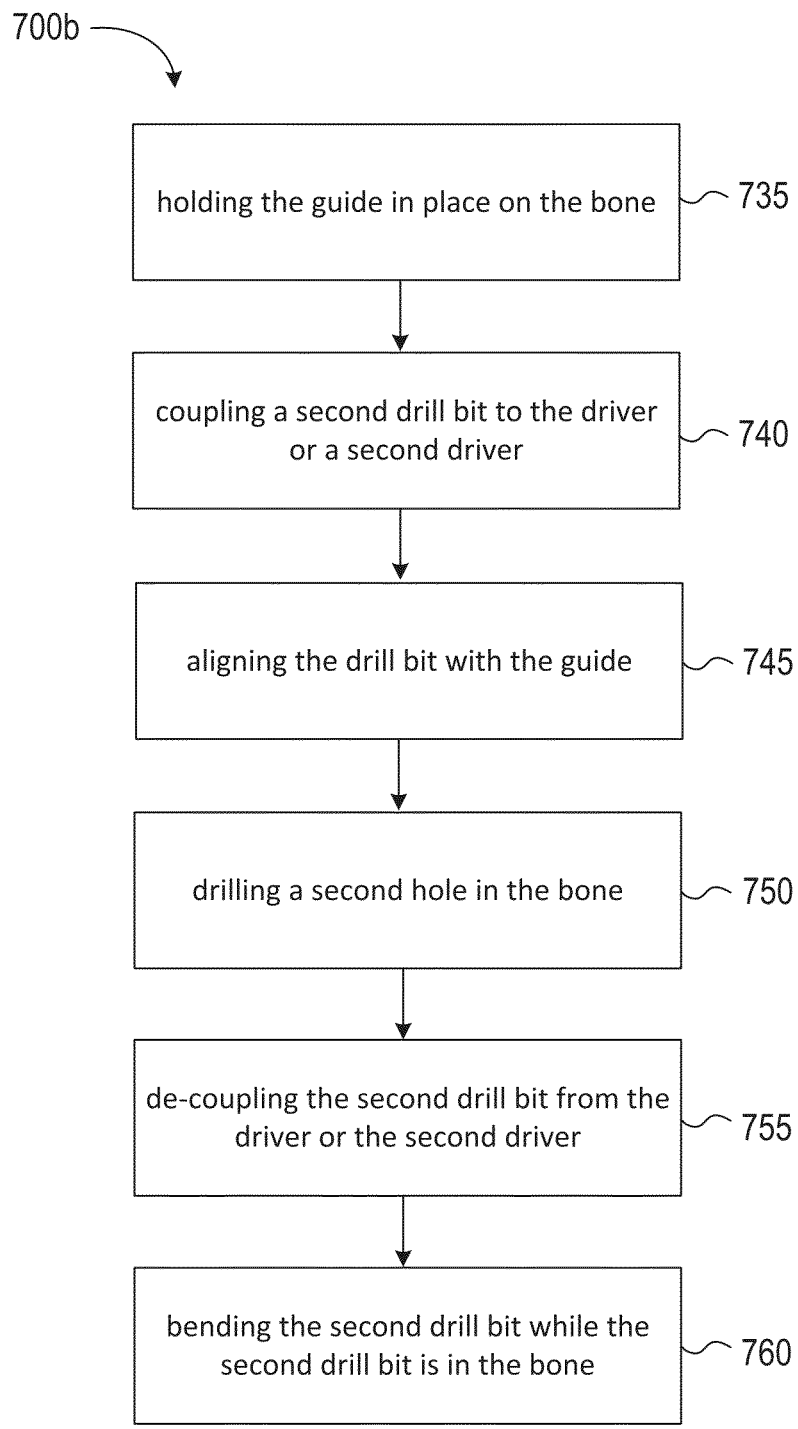

DRILL BITS AND METHODS FOR PREPARING BONE

CLAIM OF PRIORITY

This application claims the benefit of U.S. Provisional Patent Application Ser. No. 62/482,331, filed on Apr. 6, 2017, the benefit of priority of which is claimed hereby, and which is incorporated by reference herein in its entirety.

TECHNICAL FIELD

This document pertains generally, but not by way of limitation, to orthopedic devices, and, more particularly, to the orthopedic devices and methods for forming holes in bone.

BACKGROUND

Bone fractures are a common occurrence that can be treated with surgical intervention. One type of intervention used to treat bone fractures is the use of orthopedic staples (e.g., bone staples) to hold the bone fragments on either side of the fracture together. The implanted orthopedic staple helps keep the bone fragments together so that they do not drift apart, allowing the bone to heal faster and reducing the risk of the fracture propagating through the bone.

In order to implant an orthopedic staple or other fixation apparatus, the surgeon needs to prepare holes in the bone pieces on either side of the fracture site. Once the holes are prepared in the bone, a staple can then be inserted into the holes thereby implanting the staple into the bone to hold or compress the fracture site together.

The surgeon uses a drill and a drill guide to prepare the holes. It is important to hold the drill guide in alignment while drilling both of the holes. If the drill guide shifts between drilling a first hole and drilling a second hole, the holes can be misaligned and insertion of the staple can be difficult or impossible.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 5b is a close-up fragmentary view of FIG. 5a.

FIG. 5d is a top view of FIG. 5a.

FIG. 7a is a flow chart illustrating an example method of using a first drill bit to prepare a bone of a living being for fixation.

FIG. 7b is a flow chart illustrating an example method of using a second drill bit to prepare a bone of a living being for fixation. The methods of FIGS. 7a and 7b can be used alone or together.

DETAILED DESCRIPTION

As discussed above, bone fractures are a common occurrence that can be treated with surgical intervention. One type of intervention used to treat bone fractures is the use of orthopedic or bone staples that hold the bone fragments on either side of the fracture together. The implanted orthopedic staple helps to compress the bone fragments together so that they do not drift apart, allowing the bone to heal faster and reducing the risk of the fracture propagating through the bone.

In order to implant an orthopedic staple, the surgeon needs to prepare holes in the bone pieces on either side of the fracture site. The surgeon uses a drill driven by a driver to prepare the holes. In order to achieve the proper location for the holes, a drill guide can be used. It is important to hold the drill guide in alignment while drilling both of the holes. If the drill guide shifts between drilling a first hole and drilling a second hole, the holes can be misaligned and insertion of the staple can be difficult or impossible.

Improved orthopedic drills, systems and methods are described herein. An orthopedic drill bit can be used for maintaining alignment of the drill guide. The drill bits described herein can maintain alignment of the drill guide during surgery. Other surgery steps can include drilling of additional holes after the first hole, other bone preparation steps, such as sawing.

The devices, systems, and methods disclosed herein can eliminate the need for an alignment peg to be inserted after drilling a hole. More specifically, the drill bit and methods in this disclosure can eliminate the step of removing a drill bit after drilling a hole, and then having to insert an alignment peg in place of the drill bit. As a result the number of surgical steps can be reduced, thereby reducing operating room time. In addition, using the drill bit as the alignment peg can prevent the guide from becoming misaligned. In conventional surgeries the guide can become misaligned when the drill bit has been removed from the hole and the peg has not yet been inserted into the hole.

Example Drill Bit Overview

Figure 1:
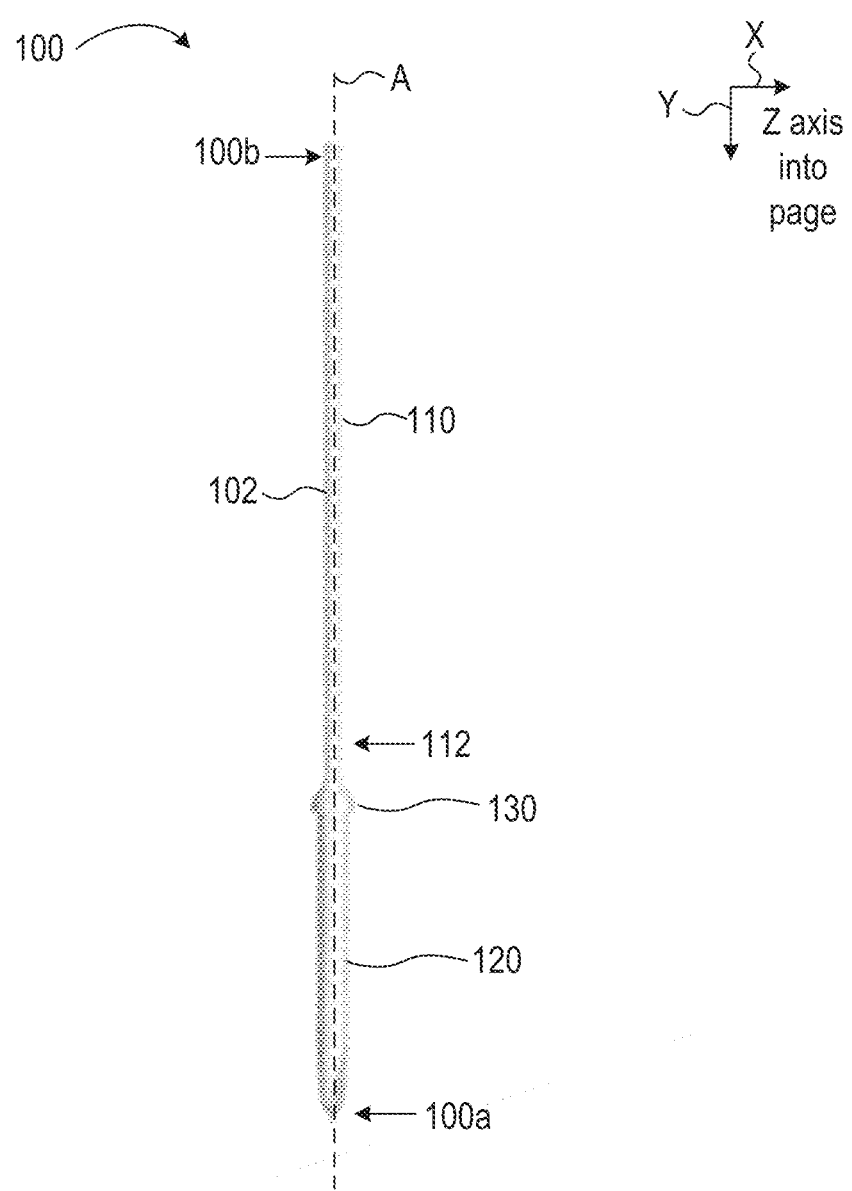
FIG. 1 is a side view of an illustrative drill bit in accordance with at least one example.

FIG. 1 is a side view of an illustrative drill bit 100 for preparing a bone of a living being to accept a fixation apparatus 400 (FIG. 6) in accordance with at least one example. The example drill bit 100 can include a body 102 extending from a proximal end 100a to a distal end 100b along a longitudinal axis A. The body 102 can include a drill bit tip 120 and a drive attachment 110. The drill bit tip 120 can be located at the proximal end 100a. The drive attachment 110 can be located more distal from the proximal end 100a than the drill bit tip 120. For example, the drive attachment 110 can be formed at the distal end 100b, or in between the drill bit tip 120 and the distal end 100b. To allow the drill bit 100 to function as an alignment peg, and remain out of the way during other work at the fixation site, the drive attachment 110 can be configured to be bent while the drill bit tip 120 is located in the prepared bone hole, and to remain in the prepared bone hole to hold the guide 300 in place while other steps of the operation are completed. Other steps in the operation can include, but are not limited to: drilling additional holes, sawing steps, or any other suitable steps.

In some examples, the drive attachment 110 can be formed of an orthopedic grade Kirschner wire. In some examples, the drive attachment 110 can have a diameter of between 0.010 to 0.200 inches. In a preferred example, the diameter can be 0.062 inches (e.g., about 0.062 inches, exactly 0.62 inches, 0.62 inches plus manufacturing tolerances). The drive attachment 110 can also be formed of a Steinmann pin. The drive attachment can be formed any suitable material such as titanium, steel and metal alloys. Suitable materials include, but are not limited to: Titanium alloy Ti-6al-4v, 316 stainless steel, 17-4 PH stainless steel, or cobalt-chromium-molybdenum (CoCrMo). Any suitable diameter and material that results in the ability to bend the drill bit 100 while it is located in the prepared bone hole can be used.

In some examples, the drive attachment 110 can be configured to be bent (e.g., 112, FIG. 4) at least 20 degrees off of the longitudinal axis A, or between about 20 degrees and about 170 degrees off the longitudinal axis A of the drill bit 100 while the drill bit tip 120 is in the prepared bone 1. In some examples, the drive attachment can be configured to be bent at least 20 degrees off of the longitudinal axis A of the drill bit 100 while the drill bit tip 120 is in the prepared bone 1. In some examples that may be more preferred examples, the drive attachment 110 can be configured to be bent at least 45 degrees off of the longitudinal axis A of the drill bit 100, or more preferably at least about 75 degrees off of the longitudinal axis A of the drill bit 100 while the drill bit tip 120 is in the prepared bone. This may provide additional flexibility to the surgeon to bend the drill bit 100 further out of the way for better access to the guide.

In some example drill bits, the force required to bend the drive attachment 110 can be less than the force required to bend the drill bit tip 120. The force required can be small enough that the drill bit 100 can be bent by hand, such as with a pliers or other tool. A force small enough to be bent by hand can be the force that an average healthy adult female, or average healthy adult male, or average healthy adult human can apply to the drill bit 100. This can be determined according to known anatomic databases or testing. The force required for bending the drive attachment 110 can be low enough that it can be accomplished while the drill bit tip 120 is in the prepared bone hole.

While the drive attachment 110 can be configured to be bent after preparing the bone and while still in the bone, the illustrative drill bit 100 should not bend while it is being used to drill a hole. The drive attachment 110, while bendable, can be configured not to bend while mounted in a mounting attachment 810 of a driver 800 (FIG. 8) and while drilling a hole in the bone. However, the drive attachment 110 can be configured to bend (e.g., 112, FIG. 4) while arranged in the prepared bone at a final position of drilling a hole in the bone and when detached from the driver 800.

Figure 3:
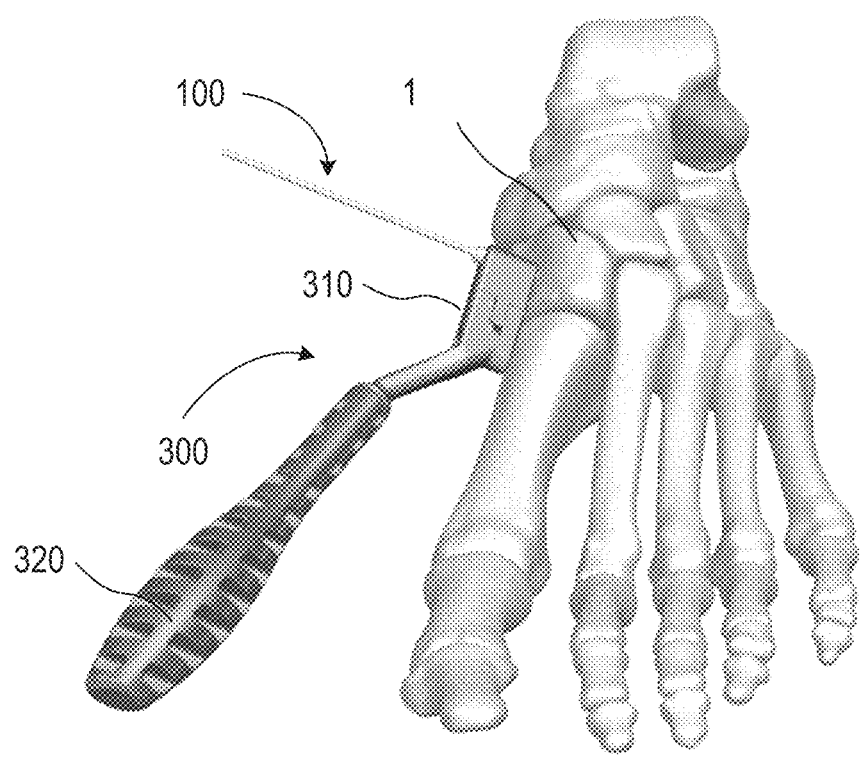
FIG. 3 is a side view of the illustrative drill bit of FIGS. 1 and 2, drilled into the bone through the guide.

As shown in FIG. 1, the example drill bit 100 can also include a collar 130 located between the drill bit tip 120 and the drive attachment 110. As shown in FIG. 3, this collar 130 can be configured to bottom out on the guide 300 when the drill bit tip 120 has reached the predetermined depth in the bone. In some examples, and as shown, a diameter of the drill bit tip 120 can be greater than a diameter of the drive attachment 110. To facilitate the collar 130 bottoming out on the guide 300, a diameter of the collar 130 can also be greater than the diameter of the drill bit tip 120.

In some examples, such as when the hole to be drilled is smaller than the diameter of Kirschner wire or Steinmann pin to be used, the drill bit tip 120 can be smaller in diameter than the drive attachment 110. In such cases, the diameter of the drill bit tip 120 can be smaller than the drive attachment 110, or the diameter of the drive attachment can be larger than the diameter of the collar 130.

Example Methods

The example methods described herein are directed to preparing a bone of a living being for fixation. The methods will be described with reference to the example drill bit 100 of FIG. 1. The example methods 700a described herein are merely illustrative in nature. Although the methods 700a can be used with the example drill bit 100 of FIG. 1, the methods 700a can also be used with other drill bits. Likewise, the example drill bit 100 of FIG. 1 can be used with other methods 700a. The example methods 700a are not limited to the steps specified herein. The methods 700a can include fewer steps or additional method 700a steps other than those described in this disclosure.

The example methods 700a will be described with respect to the steps depicted in FIGS. 2-4, 5a-5d and 6. These steps are outlined in the illustrative flow charts of the methods 700a, 700b and 700c shown in FIGS. 7a-7c, respectively. The methods 700a of 700a, 700b and 700c can be used together as one method 700a. However, the steps of the methods 700a, 700b and 700c can also be used independently or in combination with other methods 700a.

FIG. 7a is a flow chart illustrating an example method 700a of using the illustrative drill bit 100 of FIG. 1 to prepare a bone of a living being for fixation. Step 705 of the method 700a can include coupling a first drive attachment 110 of a first drill bit 100 to a mounting attachment 810 of a driver 800. For example, the drill bit 100 of FIG. 1 can be coupled to the driver 800 of FIG. 8.

In some examples of the method 700a, the first drill bit 100 can be the only drill bit. In other examples, such as the example methods of FIGS. 7b and 7c, a second drill bit 200 and/or other tools, including sawing tools, can also be employed. The additional tools can be driven with the same driver 800, such as a universal driver 800, or tools can be driven with a different driver 800. FIG. 8 is an example of a driver 800 that can be used in accordance with example drill bits and/or sawing methods 700a described herein. Various adapters can be used with the driver 800 to allow coupling to various drill bits and saw tools.

Figure 2:
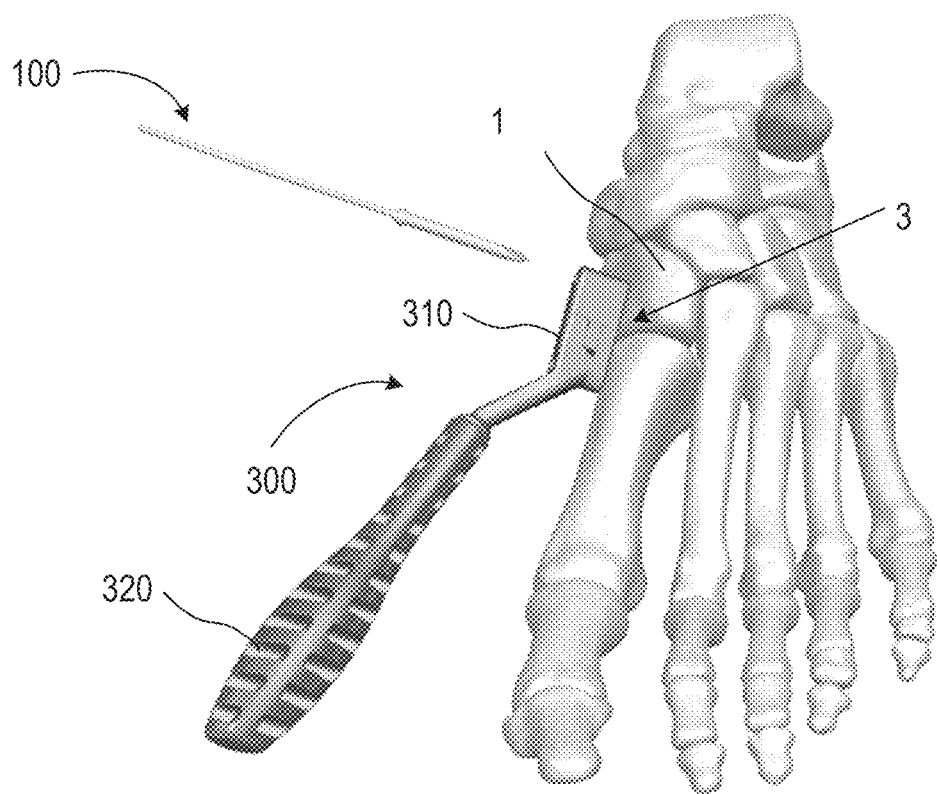
FIG. 2 is side view of the illustrative drill bit of FIG. 1 aligned with a first hole in a guide, with the drill bit and the guide placed proximate a fracture site just prior to drilling a hole in the bone.

FIG. 2, step 710 of the method 700a can include placing a guide 300 proximate a bone where a fracture site 3 is located. The guide 300 can provide positioning and alignment control while preparing the bone. The example guide 300 shown in FIG. 2 can include a guide head 310 having one or more openings 330a, 330b extending therethrough (FIG. 5d). The openings can correspond to an area of bone to be removed. In order for the surgeon to hold the guide 300 in place, a handle 320 can be configured to extend from the guide head 310. With the guide 300 in place, step 715 can include aligning the first drill bit 100 with the first hole in the guide 300.

To prepare the bone for fixation, step 720 of the method 700*a* can include removing some of the bone by drilling a hole. FIG. 3 shows a side view of the illustrative first drill bit 100 of FIG. 1 extending through an opening 330*a* of the guide 300 and drilled into the bone.

Figure 4:
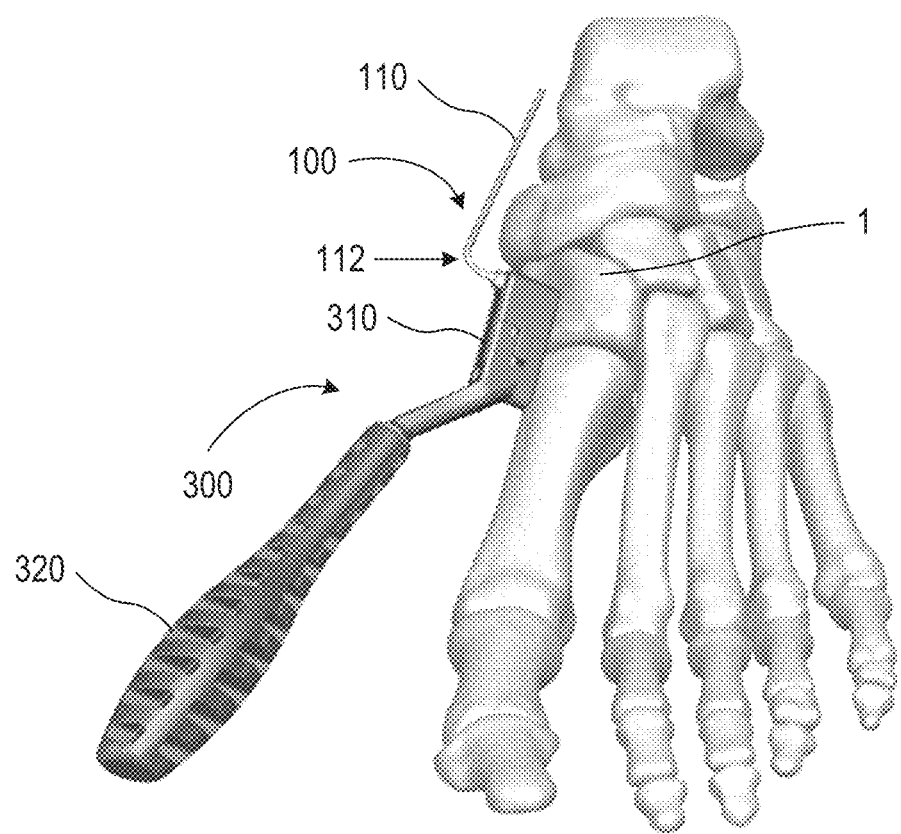
FIG. 4 is a side view of the illustrative drill bit of FIGS. 1-3 in a bent arrangement and while still located in the bone.

After the hole is prepared in the bone, step 725 of the method 700*a* can include de-coupling the first drive attachment 110 of the first drill bit 100 from the mounting attachment 810 of the driver 800, and step 730 can include bending the first drill bit 100. De-coupling the first drill bit 100 from the driver 800 can be done while the first drill bit 100 is still in the bone. FIG. 4 is a side view of the illustrative first drill bit 100 of FIG. 1 in a bent arrangement (e.g., 112) and while located in the bone and serving as an alignment peg. FIG. 4 shows the position of the first drill bit 100 after bending the first drill bit 100 at the first drive attachment 110. Bending the first drill bit 100 at the first drive attachment 110 can move the first drive attachment 110 out of the way so that the surgeon can complete other steps of the method 700*a*. This can allow the first drill bit 100 to act as an alignment peg to hold the guide 300 in place at the desired location on the bone. The drill bit 100 can be bent in accordance with the bending described with regard to the example drill bit 100 of FIG. 1. In some examples, the bending step 705 can be conducted after the first drill bit 100 has been de-coupled from the driver 800.

In some examples, bending the first drill bit 100 can include bending the first drill bit 100 at least 20 degrees off of the longitudinal axis A of the first drill bit 100. The bending may be performed while the drill bit is still in the prepared bone hole. In another example, bending the first drill bit 100 can include bending the first drill bit 100 at least 45 degrees off of the longitudinal axis A of the drill bit 100. In some applications, it may be more preferably to bend the first drill bit 100 at least 75 degrees off of the longitudinal axis A of the drill bit 100 to provide better access to the guide 300. Any amount of bending that allows access to the guide 300 for additional steps to be performed can be used, including the various amounts and ranges disclosed herein. The first drill bit 100 can be bent along the first drive attachment 110 at a location between a collar 130 (the collar 130 was previously described with respect to FIG. 1) and a distal end 100*b* of the drill bit 100.

Figure 9:
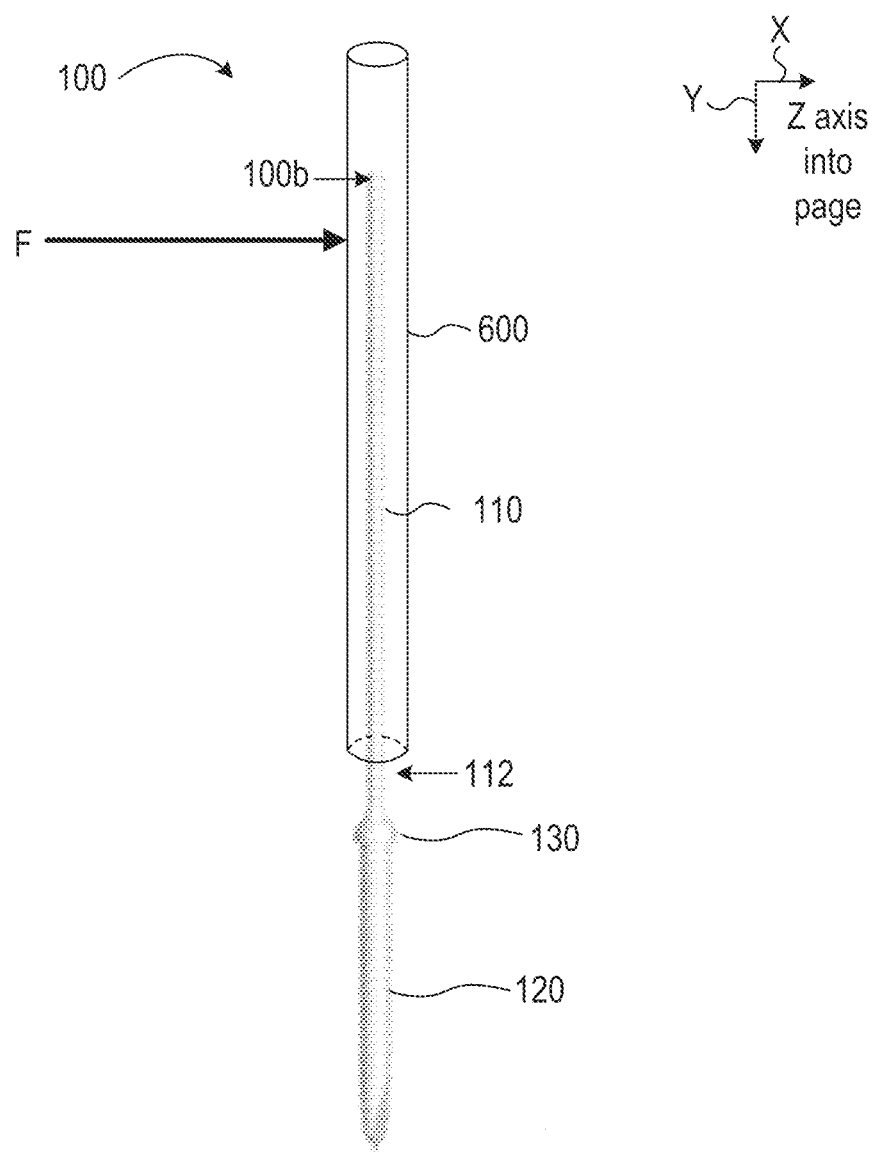
FIG. 9 is a side view of an example tool that can be inserted over the drill bit of FIG. 1 to bend the drill bit.

The first drill bit 100 can be bent with a tool, such as pliers. As shown in FIG. 9, another tool that can be used to bend the drill bit is an elongate hollow tube 600. To bend the drill bit, the elongate hollow tube 600 can be placed over the distal end 100*b* of the first drive attachment 110. The elongate hollow tube 600 can have an internal diameter larger (e.g., 101% larger to 300% larger) than the diameter of the first drive attachment 110. By placing the hollow tube over the distal end 100*b* of the first drive attachment 110 and applying a force F generally perpendicular to a longitudinal axis B of the tube 600, the force to bend the first drill bit 100 is applied in an ergonomic manner. Any suitable tool can be used to bend 112 the first drill bit 100.

Figure 5A:
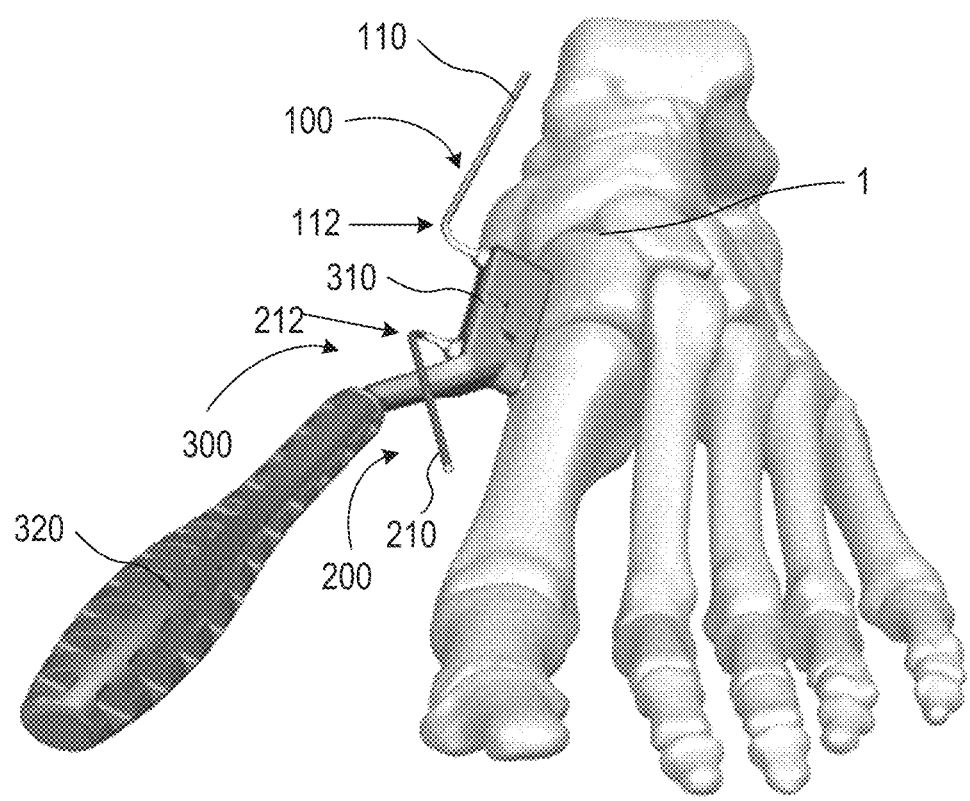
FIG. 5a is a side view of the illustrative drill bit of FIGS. 1-4, as well as a second drill bit drilled into the bone through the guide and in a bent arrangement while located in the bone.

FIG. 7*b* is a flow chart illustrating an example method 700*b* of using the illustrative second drill bit 200 of FIG. 5*a* to prepare a bone of a living being for fixation. In some examples, the methods 700*a* of FIGS. 7*a* and 7*b* can be used alone or together. Method 700*b* can be related to preparing a second hole in the bone. The steps of example method 700*b* and the second drill bit 200 can be similar to the method 700*a* and the features of the first drill bit 100 described above. The example method 700*a* can be used alone or in conjunction with example method 700*b*. Conversely, the method 700*b* can be used alone or in conjunction with the method 700*a*. For example, method 700*b* can include preparing the second hole, and can be used with a method of preparing a first hole that is different than example method 700*a*.

FIGS. 5*a*-5*d* show various views of a fracture site 3 when the methods 700*a* and 700*b* are used together to prepare both a first hole and a second hole.

FIG. 5*a* is a side view of the first drill bit 100 of FIG. 4, and including a second drill bit 200 drilled into the bone through a second hole of the guide 300. The first and second drill bits are shown in a bent arrangement while located in the bone. Like numerals of second drill bit 200 and first drill bit 100 represent like elements.

Figure 5B:
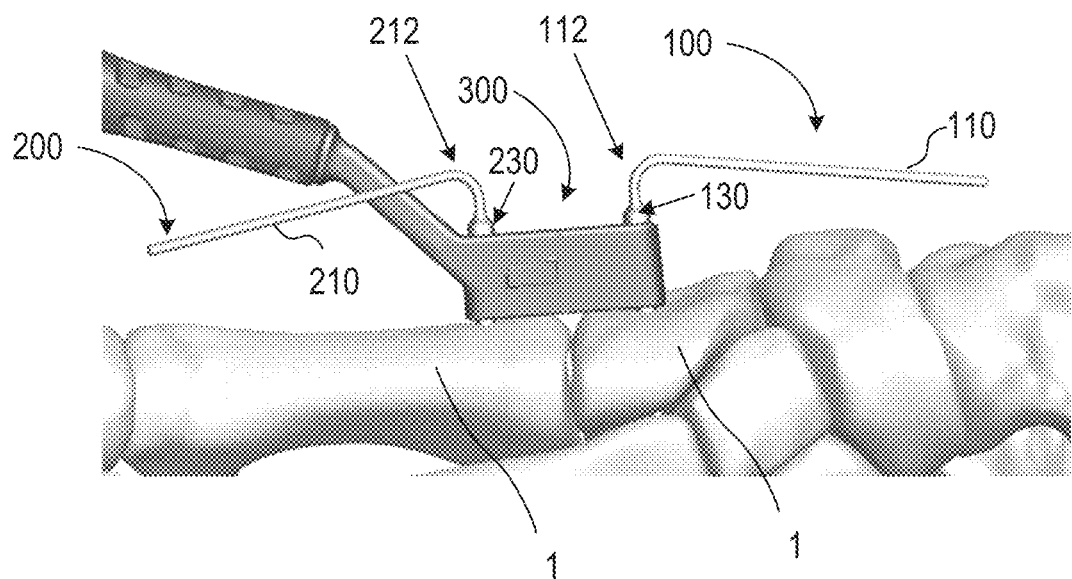
Figure 5C:
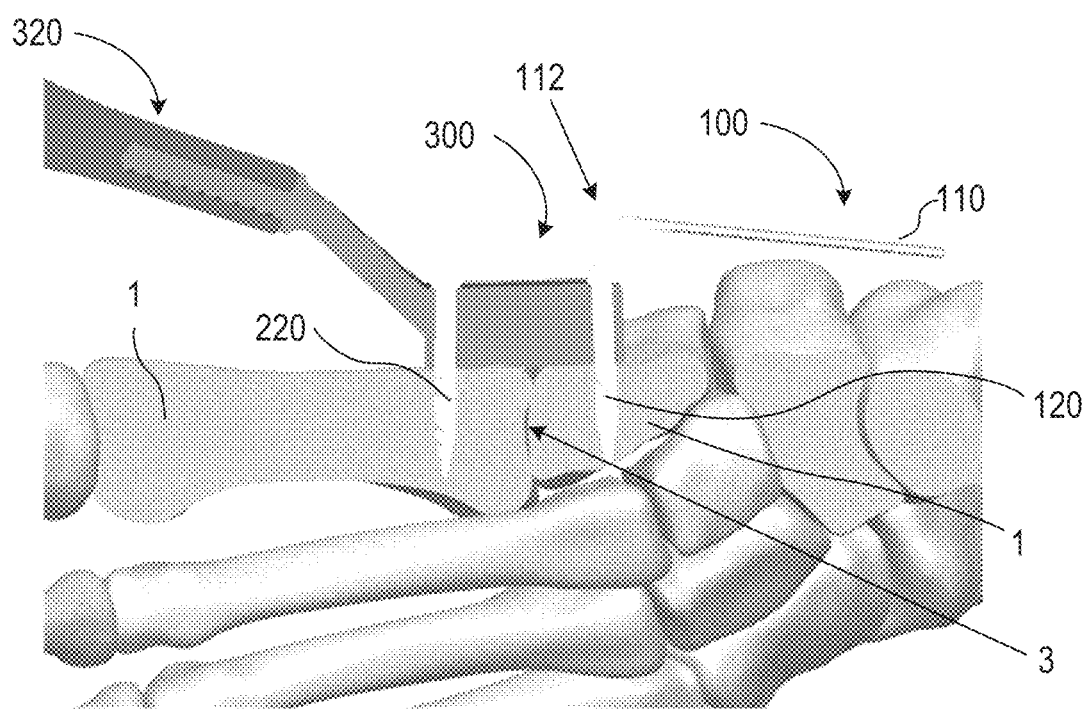
FIG. 5c is a cross-section of the close-up fragmentary view of FIG. 5b, taken along line A-A' in FIG. 5d.
Figure 5D:
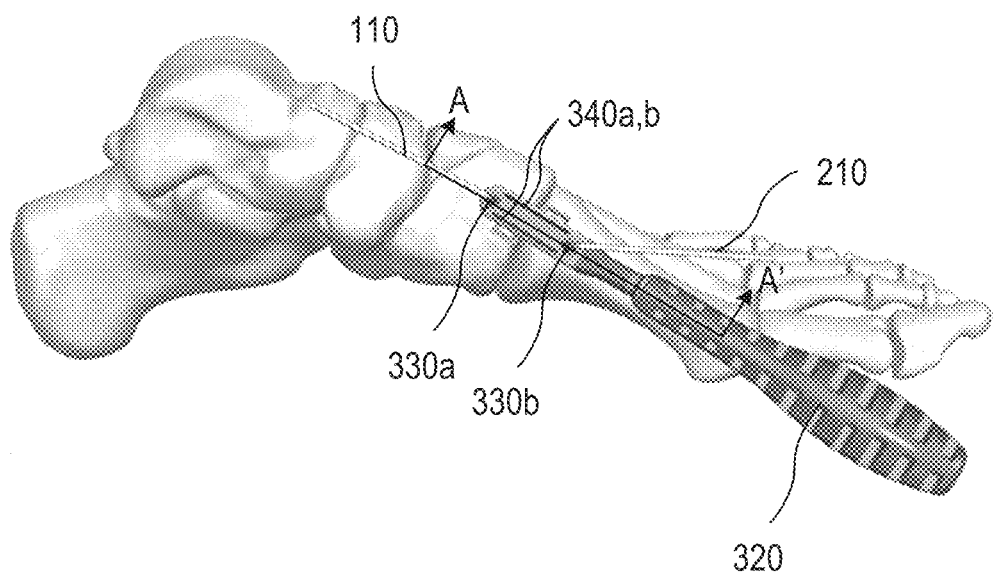

FIGS. 5*b*-5*c* show different views of FIG. 5*a*. FIG. 5*b* is a close-up fragmentary view. FIG. 5*c* is a cross-section of the close-up fragmentary view of FIG. 5*b*, as taken along line A-A' in FIG. 5*d*. Finally, FIG. 5*d* is a top view of the illustrative first and second drill bits of FIG. 5*a*.

The method 700*b* can include the surgeon holding the guide 300 in place on the bone at step 735, in preparation for drilling a second hole. Step 740 can include coupling a second drive attachment 210 of a second drill bit 200 to the mounting attachment 810 of the driver 800. In step 745, the surgeon can align the second drill bit 200 with a second opening 330*b* on the guide 300 and then in step 750 can drill a second hole into the bone. The steps of aligning the second drill bit 200 and drilling a second hole in the bone can be completed while the first drill bit 100 is still in the bone.

Upon completion of drilling the second hole, step 755 can include de-coupling the second drive attachment 210 from the mounting attachment 810 of the driver 800. Step 760 is optional depending on several factors, but can include bending the second drill bit 200 at the second drive attachment 210. As disclosed with regard to the method 700*a*, the bending and de-coupling steps can be completed while the second drill bit 200 remains in the bone. Like the bending step 705 described for the first drill bit 100, the bending step 760 for the second drill bit 200 can include bending the second drill bit 200 at least 20 degrees off of the longitudinal axis (e.g., axis A in FIG. 1) of the second drill bit 200, or at least 45 degrees off of the longitudinal axis A of the second drill bit 200, or in some applications, more preferably at least 75 degrees off of the longitudinal axis. Any suitable amount of bending, including the ranges disclosed with respect to the drill bit 100 of FIG. 1 can be used. In some cases, merely bending the drill bits a small amount, such as 20 degrees off of the longitudinal axis A, can provide the surgeon enough access to the guide 300, depending on the steps that follow and the clearance needed to access features of the guide 300.

As with the first drill bit 100, the second drill bit 200 can be bent (e.g., 212, FIG. 5*a*) along the second drive attachment 210 at a location between a collar 230 (the collar 130 was previously described with respect to FIG. 1) and a distal end of the second drill bit 200.

In a case where the methods 700*a* and 700*b* are used together, but are not followed by method 700*c*, the method 700*a* can include removing the first and second drill bits 100, 200 from the bone, and inserting a fixation apparatus 400 into the first and second holes.

As a side note, it is contemplated that in the situation where methods 700*a* and 700*b* are used together, that the second drill bit 200 could be coupled to a second driver 800, instead of coupling the second drill bit 200 to the same driver 800 that the first drill bit 100 was coupled to. This minor modification of the method 700a does not deviate from the scope of this disclosure. Whether using different drivers to complete the steps of the method 700a, or the same driver 800 to do all the steps of the method 700a, these methods 700a are considered to be equivalent to one another.

Figure 7C:
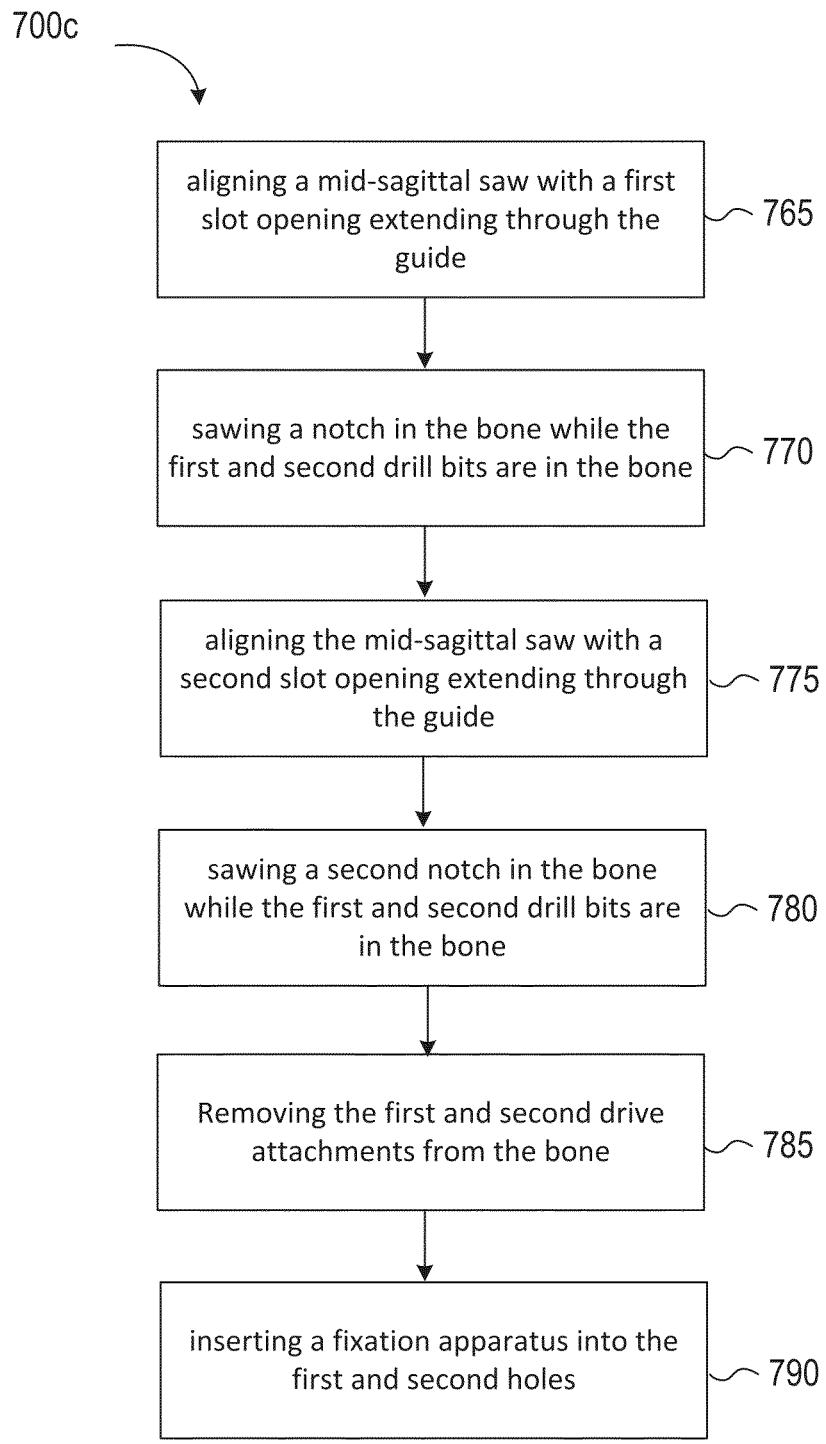
FIG. 7c is a flow chart illustrating an example method including additional method steps. The example method of FIG. 7c can be used alone or together with one or both of the methods of FIGS. 7a and 7b.
Figure 8:
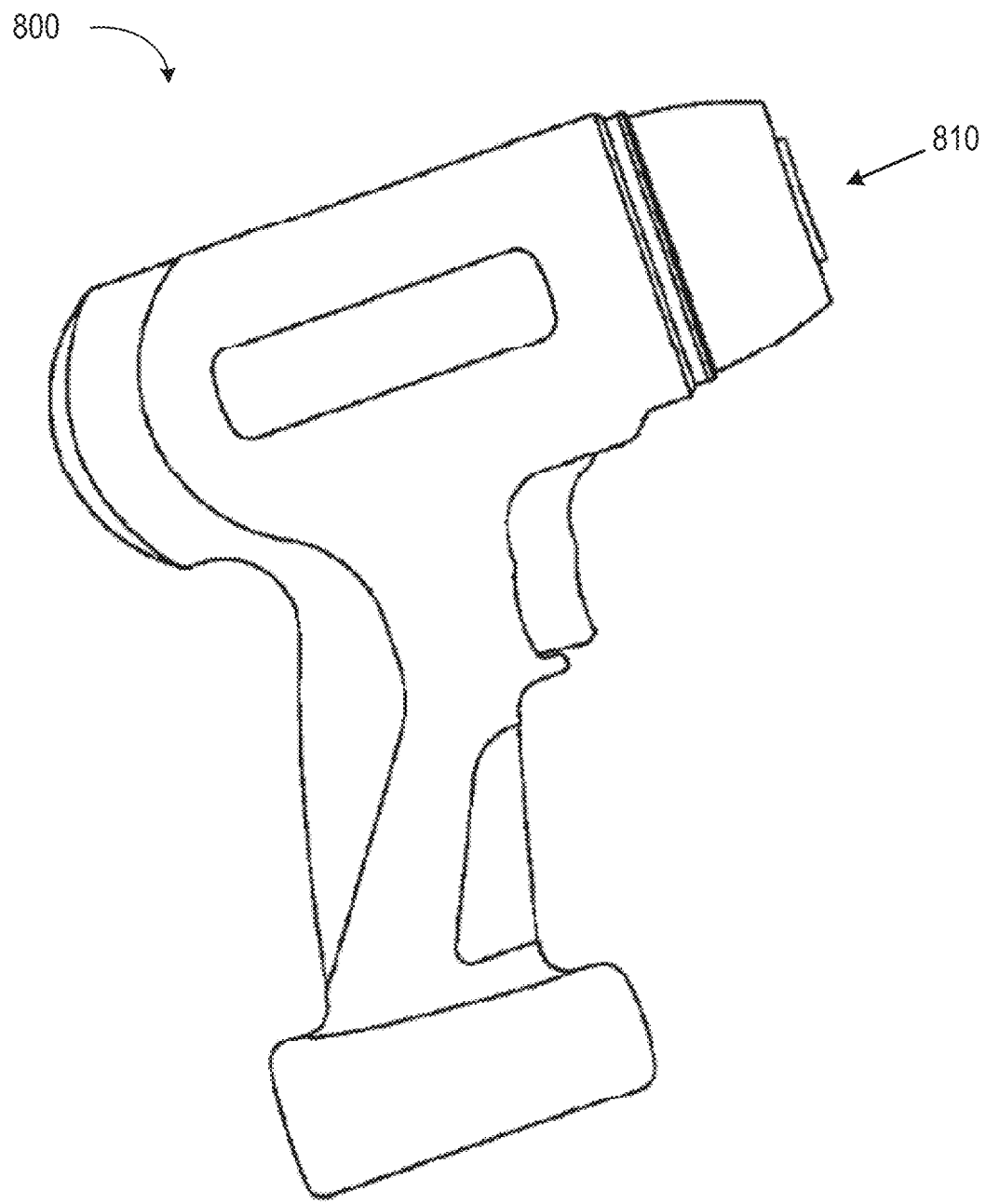
FIG. 8 is an example of a driver that can be used in accordance with example drill bits and methods described herein.

FIG. 7c is a flow chart illustrating an example method 700c including additional method steps. The example method 700c of FIG. 7c can be used alone or together with one or both of the methods 700a of FIG. 7a and/or method 700b and FIG. 7b. If the method 700c is used together with the methods 700a and 700b, the previously disclosed steps can be performed but with the first and second drill bits left in the bone to serve as alignment pegs.

For example, with the first and second drill bits 100, 200 left in place in the bone, and in a bent configuration, step 765 can include aligning a mid-sagittal saw with a first slot opening 340a extending through the guide 300. Step 770 can include sawing a first notch in the bone at the first slot opening 340a (FIG. 5d).

In addition to the first notch, a second notch can be sawed into the bone at a second slot opening 340b (FIG. 5d). To do so, the method 700a can include step 775 of aligning the mid-sagittal saw (or another saw) with a second slot opening 340b (FIG. 5d) extending through the guide 300; and step 780 can include sawing a second notch in the bone.

Figure 6:
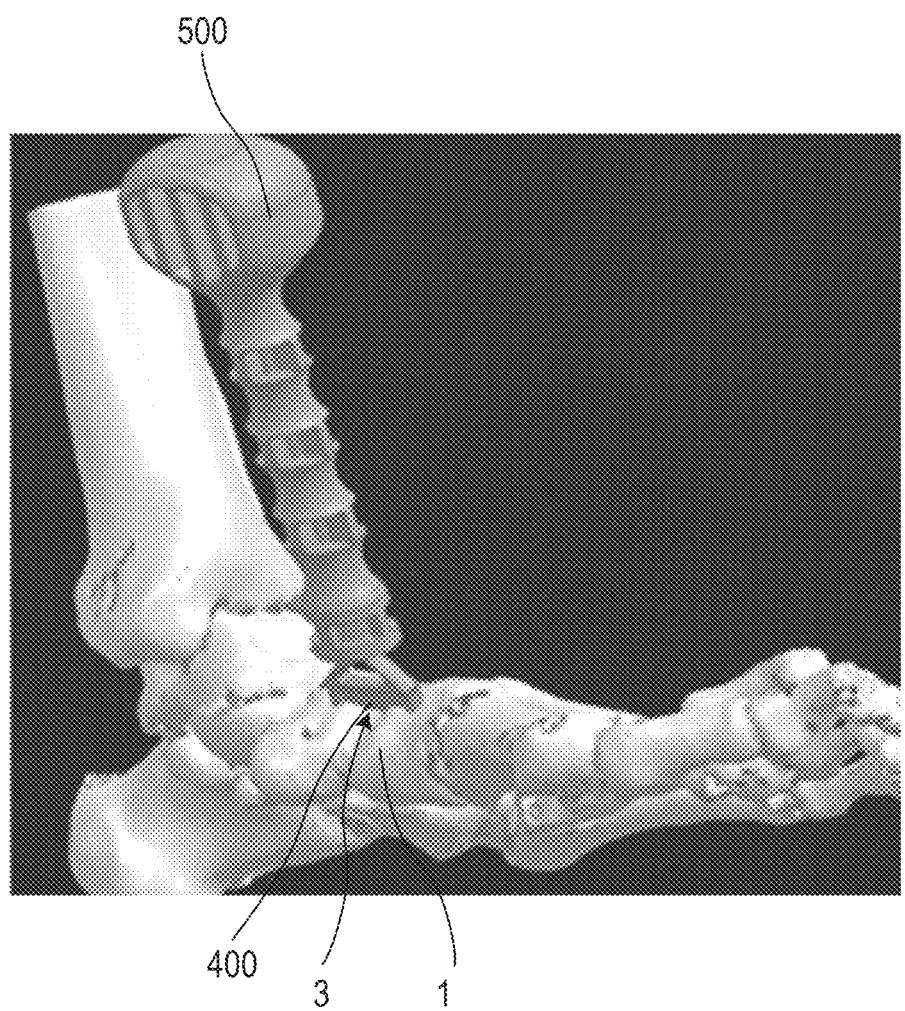
FIG. 6 is a perspective view of an insertion tool positioned proximate a fracture site and while inserting a fixation apparatus into the prepared bone.

In step 785, the first and second drill bits 100, 200 can be removed from the bone 1, and in step 790, a fixation apparatus 400 such as an orthopedic staple, can be inserted and/or impacted into the first and second holes in the bone. Insertion of the fixation apparatus 400 can be performed by hand. In some examples, and as shown in FIG. 6, insertion can also be performed by an inserter 500. The inserter 500 can be coupled to the fixation apparatus 400 to hold the fixation apparatus 400 during insertion. An impact force can be applied, such as with a mallet by tapping on the distal end of the inserter 500 opposite the fixation. Then the inserter 500 can be de-coupled from the fixation apparatus 400, leaving the fixation apparatus 400 implanted into the bone 1. At this point, fixation of the bone fracture site 3 has been achieved.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

NUMBERED EXAMPLES

Example 1 is a method of preparing a bone of a living being for fixation, the method comprising: placing a guide at a desired location on the bone, the guide having an opening extending therethrough, the opening corresponding to an area of bone to be removed; coupling a first drive attachment of a first drill bit to a mounting attachment of a driver; aligning the first drill bit with the opening on the guide; drilling a first hole in the bone; de-coupling the first drive attachment of the first drill bit from the mounting attachment of the driver while the first drill bit is in the bone; and bending the first drill bit at the first drive attachment.

In Example 2, the subject matter of Example 1 optionally includes coupling a second drive attachment of a second drill bit to the mounting attachment of the driver; aligning the second drill bit with a second opening on the guide while the first drill bit is in the bone; drilling a second hole in the bone; de-coupling the second drive attachment from the mounting attachment of the driver while the second drill bit is in the bone; and bending the second drill bit at the second drive attachment.

In Example 3, the subject matter of any one or more of Examples 1-2 optionally include coupling a second drive attachment of a second drill bit to a mounting attachment of a second driver; aligning the second drill bit with a second opening on the guide while the first drill bit is in the bone; drilling a second hole in the bone; de-coupling the second drive attachment of the second drill bit from the mounting attachment of the second driver while the second drill bit is in the bone; and bending the second drill bit at the second drive attachment.

In Example 4, the subject matter of any one or more of Examples 2-3 optionally include aligning a mid-sagittal saw with a first slot opening extending through the guide; sawing a notch in the bone while the first and second drill bits are in the bone; aligning the mid-sagittal saw with a second slot opening extending through the guide; and sawing a second notch in the bone while the first and second drill bits are in the bone.

In Example 5, the subject matter of any one or more of Examples 1-4 optionally include wherein the first drill bit extends along a longitudinal axis of the first drill bit, and wherein bending the first drive attachment comprises bending the first drive attachment at least 20 degrees off of the longitudinal axis of the first drill bit.

In Example 6, the subject matter of any one or more of Examples 1-5 optionally include wherein the first drill bit extends along a longitudinal axis of the first drill bit, and wherein bending the first drive attachment of the first drill bit comprises bending the first drive attachment at least 75 degrees off of the longitudinal axis of the first drill bit.

In Example 7, the subject matter of any one or more of Examples 2-6 optionally include wherein the second drill bit extends along a longitudinal axis of the second drill bit, and wherein bending the second drive attachment includes bending the second drive attachment at least 20 degrees off of the longitudinal axis of the second drill bit.

In Example 8, the subject matter of any one or more of Examples 1-7 optionally include wherein the first drill bit extends from a proximal end having a drill bit tip, to a distal end, and wherein the first drill bit further comprises a collar located between the drill bit tip and the first drive attachment, and wherein bending the first drill bit includes bending the first drill bit at a location between the collar and the distal end.

In Example 9, the subject matter of any one or more of Examples 2-8 optionally include removing the first and second drive attachments from the bone; and inserting a fixation apparatus into the first and second holes.

In Example 10, the subject matter of any one or more of Examples 1-9 optionally include wherein the first drive attachment is formed of a Kirschner wire or Steinmann pin.

In Example 11, the subject matter of any one or more of Examples 1-10 optionally wherein the first drive attachment has a diameter of 0.062 inches.

Example 12 is a drill bit for preparing a bone of a living being to accept a fixation apparatus, the drill bit comprising: a body extending from a proximal end to a distal end along a longitudinal axis, the body including a drill bit tip at the proximal end, and a drive attachment that is located more distal from the proximal end than the drill bit tip, and wherein the drive attachment is configured to be bent while the drill bit tip is in the prepared bone.

In Example 13, the subject matter of Example 12 optionally includes wherein the drive attachment is formed of an orthopedic grade Kirschner wire or Steinmann pin.

1. In Example 14, the subject matter of Example 13 optionally includes wherein the drive attachment is formed of Kirschner wire having a diameter of 0.062 inches.

In Example 15, the subject matter of any one or more of Examples 12-14 optionally includes wherein the drive attachment is configured to be bent at least 20 degrees off of the longitudinal axis of the drill bit while the drill bit tip is in the prepared bone.

In Example 16, the subject matter of any one or more of Examples 12-15 optionally includes wherein a force required to bend the drive attachment is less than a force required to bend the drill bit tip.

In Example 17, the subject matter of any one or more of Examples 12-16 optionally includes wherein the drive attachment is configured not to bend while mounted in a mounting attachment of a driver and drilling a hole in the bone, and is configured to bend when the drill bit tip is in the prepared bone at a final position of drilling a hole in the bone and while detached from the driver.

In Example 18, the subject matter of any one or more of Examples 12-17 optionally include a collar located between the drill bit tip and the drive attachment, wherein a diameter of the drill bit tip is greater than a diameter of the drive attachment, and wherein a diameter of the collar is greater than the diameter of the drill bit tip.

Example 19 is a method of preparing a bone of a living being for fixation, the method comprising: placing a guide at a desired location on the bone, the guide having an opening extending therethrough, the opening corresponding to an area of bone to be removed; coupling a first drive attachment of a first drill bit to a mounting attachment of a driver; aligning the first drill bit with the opening on the guide; drilling a first hole in the bone; de-coupling the first drive attachment from the mounting attachment of the driver while the first drill bit is in the bone; bending the first drill bit at the first drive attachment while the first drill bit is located in the first hole in the bone, the first drill bit serving as an alignment pin while drilling a second hole in the bone with a second drill bit; and drilling the second hole in the bone with the second drill bit.

In Example 20, the subject matter of Example 19 optionally includes removing the first and second drill bits from the bone; and inserting an orthopedic staple into the first and second holes in the bone.

What is claimed is:

1. A method of preparing a bone of a living being for fixation, the method comprising:
   placing a guide at a desired location on the bone, the guide having an opening extending therethrough, the opening corresponding to an area of bone to be removed;
   coupling a first drive attachment of a first drill bit to a mounting attachment of a driver;
   aligning the first drill bit with the opening on the guide;
   drilling a first hole in the bone;
   de-coupling the first drive attachment of the first drill bit from the mounting attachment of the driver while the first drill bit is in the bone; and
   bending the first drill bit at the first drive attachment.

2. The method of claim 1, further comprising:
   coupling a second drive attachment of a second drill bit to the mounting attachment of the driver;
   aligning the second drill bit with a second opening on the guide while the first drill bit is in the bone;
   drilling a second hole in the bone;
   de-coupling the second drive attachment from the mounting attachment of the driver while the second drill bit is in the bone; and
   bending the second drill bit at the second drive attachment.

3. The method of claim 1, further comprising:
   coupling a second drive attachment of a second drill bit to a mounting attachment of a second driver;
   aligning the second drill bit with a second opening on the guide while the first drill bit is in the bone;
   drilling a second hole in the bone;
   de-coupling the second drive attachment of the second drill bit from the mounting attachment of the second driver while the second drill bit is in the bone; and
   bending the second drill bit at the second drive attachment.

4. The method of claim 2, further comprising:
aligning a mid-sagittal saw with a first slot opening extending through the guide;
sawing a notch in the bone while the first and second drill bits are in the bone;
aligning the mid-sagittal saw with a second slot opening extending through the guide; and
sawing a second notch in the bone while the first and second drill bits are in the bone.

5. The method of claim 1, wherein the first drill bit extends along a longitudinal axis of the first drill bit, and wherein bending the first drive attachment comprises bending the first drive attachment at least 20 degrees off of the longitudinal axis of the first drill bit.

6. The method of claim 1, wherein the first drill bit extends along a longitudinal axis of the first drill bit, and wherein bending the first drive attachment of the first drill bit comprises bending the first drive attachment at least 75 degrees off of the longitudinal axis of the first drill bit.

7. The method of claim 2, wherein the second drill bit extends along a longitudinal axis of the second drill bit, and wherein bending the second drive attachment includes bending the second drive attachment at least 20 degrees off of the longitudinal axis of the second drill bit.

8. The method of claim 1, wherein the first drill bit extends from a proximal end having a drill bit tip, to a distal end, and wherein the first drill bit further comprises a collar located between the drill bit tip and the first drive attachment, and wherein bending the first drill bit includes bending the first drill bit at a location between the collar and the distal end.

9. The method of claim 2, further comprising:
removing the first and second drive attachments from the bone; and
inserting a fixation apparatus into the first and second holes.

10. The method of claim 1, wherein the first drive attachment is formed of a Kirschner wire or Steinmann pin.

11. The method of claim 1, wherein the first drive attachment has a diameter of 0.062 inches.

12. A drill bit for preparing a bone of a living being to accept a fixation apparatus, the drill bit comprising:
a body extending from a proximal end to a distal end along a longitudinal axis, the body including:
a drill bit tip at the proximal end;
a drive attachment that is located more distal from the proximal end than the drill bit tip; and
a collar located between the drill bit tip and the drive attachment, wherein a diameter of the drill bit tip is greater than a diameter of the drive attachment, and wherein a diameter of the collar is greater than the diameter of the drill bit tip, and wherein the drive attachment is configured to be bent at least 20 degrees off of the longitudinal axis of the drill bit while the drill bit tip is in the prepared bone.

13. The drill bit of claim 12, wherein the drive attachment is formed of an orthopedic grade Kirschner wire or Steinmann pin.

14. The drill bit of claim 13, wherein the drive attachment is formed of Kirschner wire having a diameter of 0.062 inches.

15. The drill bit of claim 12, wherein a force required to bend the drive attachment is less than a force required to bend the drill bit tip.

16. The drill bit of claim 12, wherein the drive attachment is configured not to bend while mounted in a mounting attachment of a driver and drilling a hole in the bone, and is configured to bend when the drill bit tip is in the prepared bone at a final position of drilling a hole in the bone and while detached from the driver.

17. A method of preparing a bone of a living being for fixation, the method comprising:
placing a guide at a desired location on the bone, the guide having an opening extending therethrough, the opening corresponding to an area of bone to be removed;
coupling a first drive attachment of a first drill bit to a mounting attachment of a driver;
aligning the first drill bit with the opening on the guide;
drilling a first hole in the bone;
de-coupling the first drive attachment from the mounting attachment of the driver while the first drill bit is in the bone;
bending the first drill bit at the first drive attachment while the first drill bit is located in the first hole in the bone, the first drill bit serving as an alignment pin while drilling a second hole in the bone with a second drill bit; and
drilling the second hole in the bone with the second drill bit.

18. The method of claim 17, further comprising:
removing the first and second drill bits from the bone; and
inserting an orthopedic staple into the first and second holes in the bone.

19. The method of claim 17, wherein drilling the first hole in the bone includes drilling the first hole in the bone until a collar of the first drill bit that is located distal of the first drive attachment, bottoms out on the guide.

\* \* \* \* \*

UNITED STATES PATENT AND TRADEMARK OFFICE
CERTIFICATE OF CORRECTION

PATENT NO. : 10,905,438 B2
APPLICATION NO. : 15/927566
DATED : February 2, 2021
INVENTOR(S) : Bryce A. Isch Page 1 of 1

It is certified that error appears in the above-identified patent and that said Letters Patent is hereby corrected as shown below:

On the Title Page

Item (73), in "Assignee", in Column 1, Line 1, delete "Bioniet" and insert --Biomet-- therefor Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*